(12) United States Patent
Shuki et al.

(10) Patent No.: US 7,326,391 B2
(45) Date of Patent: Feb. 5, 2008

(54) PROCESS FOR RECOVERY AND RECYCLE OF AMMONIA FROM A VAPOR STREAM

(75) Inventors: Albert R. Shuki, Sagamore Hills, OH (US); Kenneth P. Keckler, Naperville, IL (US); Thomas L. Bowman, League City, TX (US); Thomas L. Szabo, Aurora, IL (US)

(73) Assignee: Ineos USA LLC, Lisle, IL (US)

( * ) Notice: Subject to any disclaimer, the term of this patent is extended or adjusted under 35 U.S.C. 154(b) by 313 days.

(21) Appl. No.: 11/186,032

(22) Filed: Jul. 21, 2005

(65) Prior Publication Data

US 2006/0088461 A1    Apr. 27, 2006

Related U.S. Application Data

(60) Provisional application No. 60/590,142, filed on Jul. 22, 2004.

(51) Int. Cl.
*B01D 53/58* (2006.01)
*C07C 253/00* (2006.01)
*C07C 253/24* (2006.01)

(52) U.S. Cl. .................. 423/237; 423/238; 210/150; 210/767; 210/908; 558/319

(58) Field of Classification Search ............... 423/237, 423/238; 210/767, 150, 908; 558/319
See application file for complete search history.

(56) References Cited

U.S. PATENT DOCUMENTS

| 2,797,148 | A | * | 6/1957 | Carlson | 423/352 |
| 3,985,863 | A | * | 10/1976 | Rice et al. | 423/352 |
| 4,009,243 | A | * | 2/1977 | Weber et al. | 423/234 |
| 4,259,302 | A | * | 3/1981 | Katz et al. | 423/237 |
| 4,287,162 | A | * | 9/1981 | Scheibel | 423/238 |
| 5,895,635 | A | * | 4/1999 | Brazdil et al. | 423/238 |
| 2001/0006614 | A1 | * | 7/2001 | Nero et al. | 423/238 |

* cited by examiner

*Primary Examiner*—Timothy C. Vanoy
(74) *Attorney, Agent, or Firm*—David P. Yusko

(57) ABSTRACT

A process for the recovery of unreacted ammonia from the effluent from a reaction zone used to produce acrylonitrile or methacrylonitrile comprising quenching the reactor effluent with an aqueous solution of ammonium phosphate in at least two stages, thereby capturing the ammonia component of the effluent. The captured ammonia may be recovered by heating the aqueous ammonium phosphate, which then may be recycled. Contaminants present in the aqueous ammonium phosphate may be removed, for example by solvent extraction or wet oxidation, prior to recycle.

23 Claims, 3 Drawing Sheets

PROCESS FOR RECOVERY AND RECYCLE OF AMMONIA FROM A VAPOR STREAM

BACKGROUND OF THE INVENTION

This invention is directed to recovery of ammonia from a vaporous process stream such as, for example, the reactor effluent from a hydrocarbon ammoxidation reactor. More particularly, the invention is directed to an improved process for the recovery of ammonia contained in the effluent stream from a reactor employed in the catalytic ammoxidation of propylene, propane, isobutane or isobutylene in the production of acrylonitrile or methacrylonitrile.

The processes widely used in commercial practice for recovering the products of hydrocarbon ammoxidation generally comprise the steps of: a) contacting the effluent from an ammoxidation reactor in a quench tower with an aqueous quench liquid to cool the gaseous effluent; b) contacting the quenched effluent with water in an absorber, forming an aqueous solution comprising the ammoxidation products; c) subjecting said aqueous solution to a water extractive distillation, and d) removing a first overhead vapor stream comprising acrylonitrile or methacrylonitrile and some water from the top of the column, and collecting a liquid waste stream containing water and contaminants from the bottom of said column. Further purification of the nitrile may be accomplished by passing the overhead vapor stream to a second distillation column to remove at least some impurities from the crude nitrile, and further distilling the partially purified nitrile in a third distillation column to obtain the purified acrylonitrile or methacrylonitrile.

Hydrocarbon ammoxidation, particularly of alkanes, is typically conducted using substantial excesses of ammonia. Ammonia that is not consumed in the ammoxidation exits in the reactor effluent, together with nitrile monomer and reaction by-products, including hydrocyanic acid, cyanoalkane and the corresponding aldehyde and the like. The by-products react with nitrile monomer in the presence of ammonia, or react with one another. It is therefore necessary to separate the ammonia from the effluent stream immediately after exiting the ammoxidation reactor. Conventionally, the unreacted ammonia is captured in the quench operation, step a), by including sufficient acid in the aqueous quench liquid to neutralize the excess ammonia. The aqueous bottoms comprising the corresponding salt together with other water-soluble by-products and contaminants may be removed from the quench tower, combined with other by-product streams produced in the process and recovered or prepared for disposal in an environmentally safe manner.

Alternatively, recovering the ammonia for further use may be of considerable importance to the overall process economics. Methods for regenerating the captured ammonia for recycle have been disclosed in the art.

Great Britain Patent 222,587 discloses a process for capture of ammonia from an ammonia-containing gas mixture utilizing an aqueous phosphoric acid, an aqueous solution of ammonium dihydrogen phosphate $((NH_4)H_2PO_4)$, or mixtures thereof. The ammonia is recovered by thermally decomposing the ammonium phosphate mixture. The residue is then dissolved in water to regenerate the ammonium phosphate solution.

U.S. Pat. Nos. 2,797,148 and 3,718,731 are directed to the recovery of ammonia from a process stream in the production of HCN. Generally described, the ammonia-containing gas is contacted with a 25% to 35% by weight ammonium phosphate solution having a pH of about 6 at a temperature of from 55° C. to 90° C. Ammonia regeneration is effected by contacting the resulting phosphate solution with steam.

In U.S. Pat. No. 5,895,635 there is disclosed a recovery process wherein effluent from an alkane ammoxidation reactor is passed into a quench tower and contacted with an aqueous ammonium phosphate quench solution. The quench solution will comprise monoammonium phosphate and may further comprise phosphoric acid and diammonium phosphate, and have a ratio of ammonium ions $(NH_4^+)$ to phosphate ions $(PO_4^{-3})$ of from about 0.7 to about 1.3, at a pH of from about 2.8 to about 6. The ammonia in the process stream is absorbed in the quench solution, reacting with the monoammonium phosphate component and forming diammonium phosphate. Heating the diammonium phosphate in a separate operation decomposes the diammonium phosphate, reforming the aqueous monoammonium phosphate solution and generating a vapor stream containing ammonia for recycle or recovery.

U.S. Pat. No. 5,895,635 further discloses methods for treating the aqueous phosphate solution including subjecting the aqueous monoammonium phosphate solution to wet oxidation at an elevated temperature and pressure to remove heavy organics and other objectionable contaminants prior to recycle as quench liquid. According to patentees, excess water may also be removed as needed from the ammonium phosphate solution either with the ammonia vapor stream during the decomposition step or by passing the aqueous stream exiting the wet oxidation process through evaporation means before recycle in the quench operation. Such further treatment may significantly reduce the volume of aqueous waste requiring disposal and further reduce operating costs.

The recovery and treatment methods heretofore disclosed in the art require further improvement to overcome inefficiencies and provide a more environmentally acceptable aqueous waste stream. For example, where an ammonium phosphate quench solution is employed, the residuals stream from the quench operation may retain as much as about 5% of the recoverable ammonia present in the reactor effluent stream; contaminants that remain in aqueous solution after the ammonia stripping operation may be carried into the ammonia stream from the decomposer and then into the wastewater stream, adding to the waste disposal burden; and although wet oxidation may be very effective for destroying the heavy organic components of the quench stream, wet oxidation is costly, and its use will typically be limited to reducing the contaminants to a level acceptable for recycle, for example, by treating only a fraction of the quench stream. Because of these and further inefficiencies in the methods disclosed in the art for ammonia recovery, it is desirable to have an improved method for ammonia recovery for use, for example, in the ammoxidation processes employed for the production of nitrile monomers. This invention provides such improved methods. The improvement in the efficiency of the recovery and treatment methods provided by this invention will thus be an important advance in the ammoxidation process art.

SUMMARY OF THE INVENTION

This invention is directed to recovering ammonia from a vaporous process stream such as, for example, the reactor effluent or product stream comprising the products, co-products and unconsumed reactants of a hydrocarbon ammoxidation process. The invention may be further described and characterized as an improved process for the recovery of ammonia contained in the vaporous effluent from an ammoxidation reactor employed in the catalyzed ammoxidation of propane or propylene to produce acrylonitrile, or of isobutane or isobutylene to produce methacrylonitrile.

Generally described, the improved process comprises quenching said reactor effluent, a gas or vapor comprising nitrile monomer and unreacted ammonia, with aqueous ammonium phosphate in at least two stages. In the first quench stage, the reactor effluent is passed to suitable first quench means comprising a gas-liquid contactor, for example a quench tower, and contacted with an aqueous solution comprising ammonium dihydrogen phosphate and diammonium hydrogen phosphate suitably having a first ratio of ammonium ions ($NH_4^+$) to phosphate ions ($PO_4^{-3}$) of, for example, at least about 1.3 but not more than about 2 as a first quench liquid. Typically, more than about 90% of the ammonia contained in the reactor effluent will be absorbed by said first quench liquid, raising the pH of the solution and reacting with ammonium dihydrogen phosphate to form diammonium hydrogen phosphate. The ammonia-enriched ammonium phosphate solution will be collected as quench bottoms and passed to means for removing contaminants and further to means for decomposing diammonium phosphate and recovering the captured ammonia.

The effluent, now comprising nitrile monomer and co-products together with residual ammonia, is collected as overhead and passed from the first quench means to suitable second quench means comprising a gas-liquid contactor, for example a quench tower, and contacted with an aqueous solution comprising ammonium dihydrogen phosphate having, preferably, a second ratio, of ammonium ions ($NH_4^+$) to phosphate ions ($PO_4^{-3}$) that is preferably lower than the first ratio, and can be, for example, of at least about 0.7, suitably in a range from about 0.7 to about 1.3 and preferably from about 1.0 to about 1.1, as a second quench liquid. The residual ammonia absorbed by said second quench liquid reacts with ammonium dihydrogen phosphate to form diammonium hydrogen phosphate, thereby raising the pH of the solution and providing aqueous ammonium phosphate solution having a ratio of ammonium ions ($NH_4^+$) to phosphate ions ($PO_4^{-3}$) of at least about 1.0, and preferably not more than about 1.1. The ammonia-enriched solution will be collected as second quench bottoms and passed to the first quench means as first aqueous quench liquid.

Quenching the effluent in two stages according to the invention substantially improves the recovery of ammonia, thereby reducing raw material costs.

The process economics may be additionally benefited by further process modifications to remove cyanide and organic contaminants from the aqueous ammonium phosphate before recycle and to reduce the level of contaminants in the aqueous waste stream.

DETAILED DESCRIPTION OF THE INVENTION

Figure 1:
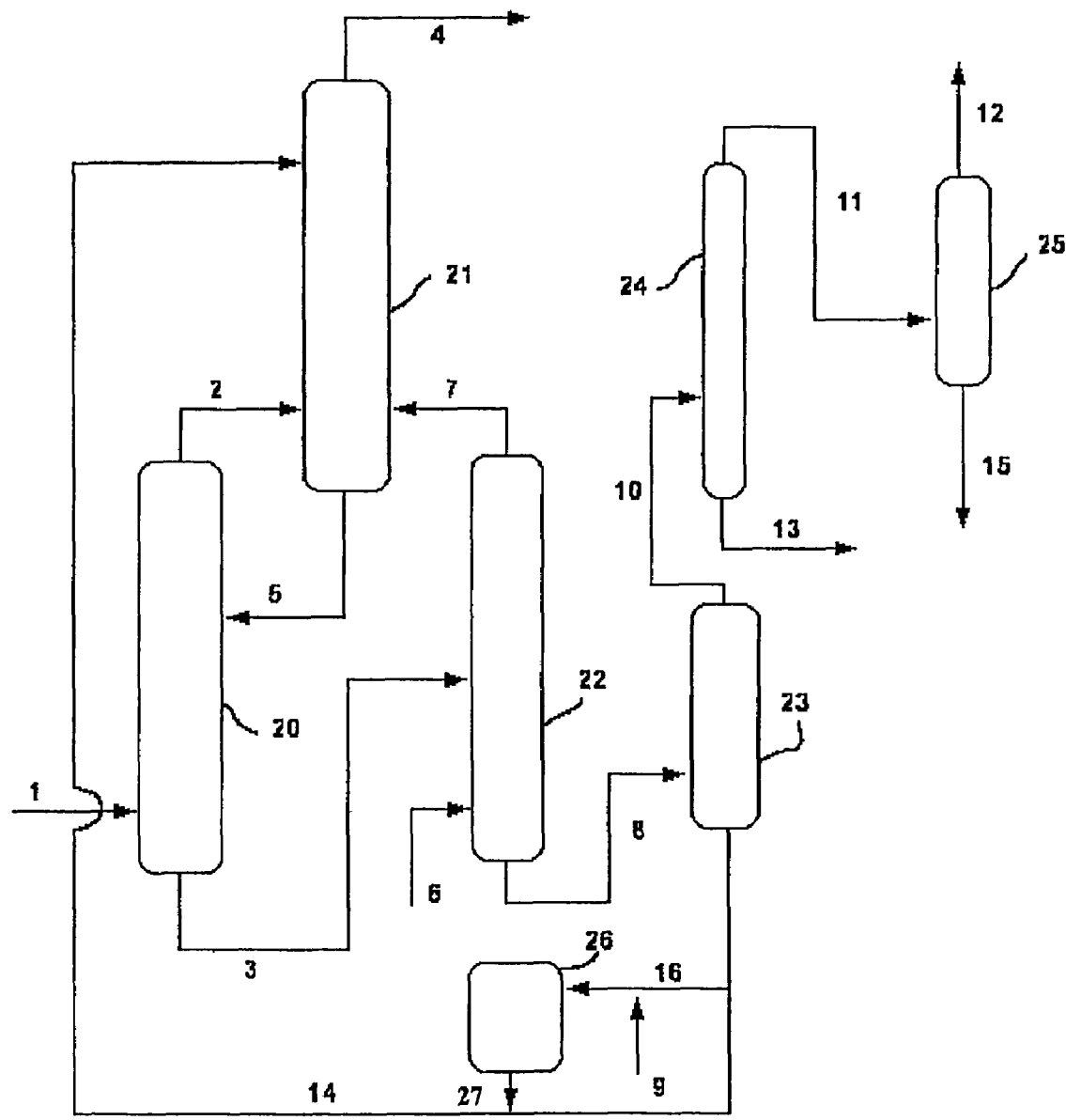
FIG. 1 is a flow diagram of a preferred embodiment of an ammonia recovery process wherein a reactor effluent is quenched in at least two stages and the organic contaminants are removed from the quench bottoms by wet oxidation prior to thermally regenerating the ammonium phosphate solution for recycle.

The improved process of this invention comprises the steps of capturing the ammonia component of a vaporous or gaseous effluent from the catalyzed ammoxidation of a hydrocarbon by quenching the effluent in two stages using aqueous ammonium phosphate; recovering the captured ammonia from the aqueous ammonium phosphate quench liquid; and regenerating and recycling the quench liquid.

In the first quench stage, reactor effluent comprising nitrile monomer and unreacted ammonia is passed to a first quench tower and contacted with a first aqueous ammonium phosphate solution at a temperature in the range of from about 40° C. to about 80° C., preferably from about 50° C. to about 65° C., said first aqueous phosphate solution comprising ammonium dihydrogen phosphate and diammonium hydrogen phosphate and having a ratio of ammonium ions ($NH_4^+$) to phosphate ions ($PO_4^{-3}$) greater than about 1.3 but not more than about 2, preferably from about 1.4 to about 1.8, still more preferably from about 1.4 to about 1.6, with a pH of from about 5 to about 7.

Most of the ammonia, typically greater than about 90%, preferably greater than 92% of the ammonia contained in the reactor effluent will be captured by being absorbed by the first quench liquid, reacting with the ammonium dihydrogen phosphate to form diammonium hydrogen phosphate and raising the pH of the quench liquid. The ammonia-rich quench liquid removed from the quench tower as first quench bottoms is passed to means for recovering the captured ammonia and means for removing contaminants.

In the second quench stage, depleted effluent comprising nitrile monomer, hydrocyanic acid and residual ammonia removed as overhead from the first quench tower is passed to a second quench tower and contacted with second quench liquid comprising aqueous ammonium dihydrogen phosphate at a temperature in the range of from about 40° C. to about 80° C., preferably from about 50° C. to about 65° C., more preferably from about 55° C. to about 60° C., thereby capturing the balance of the ammonia remaining in the effluent stream. Said second quench liquid will have a ratio of ratio of ammonium ions ($NH_4^+$) to phosphate ions ($PO_4^{-3}$) of at least about 0.7, suitably in a range from about 0.7 to about 1.3 and preferably from about 1.0 to about 1.1. An aqueous solution comprising ammonium dihydrogen phosphate and, optionally, phosphoric acid, having a pH of from about 2.5 to about 4.5, preferably from about 3 to about 4, and containing up to about 40% by weight, preferably up to about 35% by weight, more preferably from about 25 to about 35% by weight phosphate will be suitable for use as the second quench liquid in the practice of this invention.

The aqueous second quench liquid may be continuously cycled through the second quench tower, capturing ammonia until the ratio of ammonium ions ($NH_4^+$) to phosphate ions ($PO_4^{-3}$) is about 1.0 to about 1.1, then removed as quench bottoms and passed to the first quench operation as first aqueous quench liquid.

The quench means or gas-liquid contactors employed in each of the two quench stages as set forth above are quench towers. Preferably, the gas-liquid contactors will be spray towers, the quench liquid being introduced through a supply line fitted with spray nozzles or similar means for uniformly dispersing the quench liquid in the gas stream. The spray nozzles will preferably be disposed within the towers above the entry point for the effluent gas stream, directing the flow of quench liquid countercurrent to the flow direction of the effluent gas.

A variety of other gas-liquid contactors including packed columns, baffled columns, spray towers and the like are known in the art, and many of these may be found suitable for use in the invented process. It will be understood that the two quench stages may also be carried out in a single vessel, for example, a quench tower comprising communicating upper and lower quench chambers, each chamber fitted with a supply line and spray nozzles, wherein the effluent entering the bottom of the lower chamber will flow upward, encounter the first quench stage liquid, and then pass to the upper quench chamber and encounter the second quench stage liquid.

The substantially ammonia-free product stream removed from the second quench tower as overhead is passed to means for recovering the nitrile monomer and co-products. Methods for recovering and purifying these components are widely known and well described in the art, for example in U.S. Pat. No. 3,936,360, incorporated herein by reference. Generally described, processes commonly employed for this purpose typically include the step of scrubbing the vaporous effluent to absorb the monomer, then separating and purifying the monomer by extractive distillation followed by fractionation.

The ammonia-rich quench liquid removed from the quench tower as first quench bottoms will be passed to means for recovering the captured ammonia by thermally decomposing the diammonium phosphate component, providing a vapor stream comprising ammonia and an aqueous ammonium phosphate stream having a low ratio of ammonium ions ($NH_4^+$) to phosphate ions ($PO_4^{-3}$) for recycle. However, the quench bottoms will also comprise contaminants including residual monomer, cyanides and organic co-products, polymeric by-products and the like. Recycling the regenerated aqueous ammonium phosphate as quench liquid will concentrate these contaminants to unacceptable levels, interfering with further recycle. Moreover, their buildup in the waste stream creates further disposal problems. It is thus desirable to provide means for removing or significantly reducing the level of these contaminants in order for the regenerated phosphate solution to be suitable for recycle as quench liquid.

In one embodiment, more fully described and characterized below in connection with FIG. 1, stripping means will be employed to remove volatile components from the quench bottoms before thermally regenerating the quench solution. In addition, wet oxidation means will be employed to decompose and remove at least a portion of the remaining contaminants including heavy organics from the aqueous ammonium phosphate prior to recycle as second quench liquid.

Typically, the first quench liquid will be stripped in a conventional stripping tower, using a stripping gas preferably selected from the group consisting of propane, nitrogen, carbon dioxide, carbon monoxide and mixtures thereof. The stripping gas may be collected from the stripping tower as overhead, passed to a quench tower for further recovery of useful components, then separated and recycled as stripping gas.

After the volatile components are removed, the quench bottoms are thermally decomposed to liberate the captured ammonia. Stripped quench bottoms comprising enriched ammonium phosphate solution, i.e. having a ratio of ammonium ions ($NH_4^+$) to phosphate ions ($PO_4^{-3}$) greater than 1.3, are heated at ambient pressure or under an elevated pressure of up to about 900 psig, preferably in a range of about 300 to about 600 psig, in a vessel or phosphate decomposer to a temperature in the range of from 100° C. to 300° C. and held for a period sufficient to decompose at least a portion of the diammonium phosphate in the aqueous ammonium phosphate to monoammonium phosphate. A vapor phase comprising ammonia and water vapor can be collected from the decomposer as overhead and can be passed to means for rectifying the ammonia and removing water, providing ammonia, such as substantially anhydrous ammonia, for recycle. The aqueous ammonium phosphate solution collected as decomposer bottoms will have an ammonium ions ($NH_4^+$) to phosphate ions ($PO_4^{-3}$) ratio of at least about 0.7, preferably from about 0.7 to about 1.1, suitable for use as the second aqueous quench liquid in the second quench stage. The amount of water removed from the decomposer as water vapor will be sufficient to raise the solids content of the aqueous ammonium phosphate solution to a level suitable for recycle, generally from about 25 wt. % to about 45 wt. %.

Non-volatile contaminants and polymeric by-products remaining in the stripped quench bottoms and carried forward through the decomposer in the aqueous phase may be destroyed by subjecting the aqueous ammonium phosphate solution to a wet oxidation step. Suitable wet oxidation processes are well known in the art. Typically, wet oxidation will be carried out by mixing the aqueous solution with a source of oxygen in a wet oxidation reactor, for example a pipe reactor, optionally a baffled pipe reactor, and heating under pressure of from about 600 to 3000 psig at a temperature of from about 200° C. to about 650° C., preferably from about 300° C. to about 600° C. The source of oxygen is suitably a gas comprising molecular oxygen, such a pure or substantially pure molecular oxygen, or air. The organic and other oxidizable components of the solution are destroyed, forming $CO_2$, water, and other oxidation products. If shortened reaction times are desired, the oxidation may be carried out using typical wet oxidation catalysts, e.g. soluble salts of copper and iron, oxides of copper, zinc, manganese and cerium and noble metals, that are well known and widely disclosed in the art, for example in Ind. Eng. Chem. Res., 1995 Vol. 34, Pages 2-48, incorporated by reference herein. Substantially complete oxidation of the organic components may be accomplished using high temperatures and lengthy residence times. It may be desirable for economic reasons to subject only a portion of the aqueous ammonium phosphate solution to wet oxidation, thereby reducing the contaminants to a level acceptable for recycle, rather than seeking complete removal. The effluent from the wet oxidation reactor will be cooled and, where appropriate, recombined with the balance of the aqueous ammonium phosphate solution for recycle to the second quench tower as said second quench liquid.

It may be desirable to further reduce the water content of the effluent from the wet oxidation reactor by passing the effluent under elevated pressure and temperature to evaporator means, for example a flash evaporator apparatus, to cool and separate the aqueous ammonium phosphate. The vapor stream from the evaporator, comprising volatiles including carbon dioxide and excess water, may be passed to the phosphate decomposer, combined with the vapor phase and passed to the ammonia rectifying means.

Alternatively, as further described below in connection with FIG. 2, the wet oxidation and thermal regeneration steps may be carried out in a single apparatus by combining the stripped quench bottoms with a source of oxygen, passing the stream to a suitable reactor, simultaneously oxidizing the contaminants and thermally decomposing the diammonium phosphate utilizing typical wet oxidation conditions. The source of oxygen is suitably a gas comprising molecular oxygen, such as air. A combined process for wet oxidation and thermal decompositon is disclosed in U.S. Pat. No. 5,895,635.

The reactor bottoms from the reactor will comprise aqueous ammonium phosphate solution having a solids content appropriate for recycle, generally from about 25 wt. % to about 45 wt. %. The vapor phase will include ammonia and water vapor from the decomposition of ammonium phosphate together with carbon dioxide and water from the wet oxidation and may thus comprise mixed ammonium carbonates as the reaction product of these components. The vapor phase may be fed directly to an ammonia rectifying means, stripped to remove water, and dehydrated, providing ammonia, such as substantially pure, anhydrous ammonia, for recycle.

Turning now to the drawing, FIG. 1, showing a flow diagram of a two-stage quench process with subsequent stripping and regeneration of the quench liquid. As seen in FIG. 1, effluent from an ammoxidation reactor (not shown) is passed via line 1 into a first quench tower 20. In first quench tower 20 the reactor effluent comprising nitrile monomer and unreacted ammonia is contacted with a first quench liquid fed by line 5. The first quench liquid, comprising ammonium phosphate solution having a ratio of ammonium ions ($NH_4^+$) to phosphate ions ($PO_4^{-3}$) of at least about 1.3 but not more than about 2, absorbs and removes ammonia from the effluent and produces an overhead stream of depleted effluent comprising crude nitrile monomer and residual ammonia, and a first quench bottom solution containing enriched ammonium phosphate solution having an increased ratio of ammonium ion to phosphate ion. The depleted effluent stream passes by line 2 to a second quench tower 21; the first quench bottom solution exits the bottom of first quench tower 20 and passes via line 3 to a quench stripper 22. Although not shown in FIG. 1, at least a portion of first quench liquid can, and preferably is, re-circulated within first quench tower 20 by, for example, using another line to direct at least a portion of the first quench bottom solution in line 3 to the upper portion of first quench tower 20 through, for example, line 5.

The overhead or depleted effluent stream entering second quench tower 21 via line 2 is contacted with a second quench liquid fed by line 14. This second quench liquid, comprising ammonium phosphate solution having an ammonium ion ($NH_4^+$) to phosphate ion ($PO_4^{-3}$) ratio of at least about 0.7, suitably in a range from about 0.7 to about 1.3, preferably from about 1.0 to about 1.1, absorbs the residual ammonia and produces an overhead stream comprising crude nitrile monomer and an ammonium phosphate solution having an increased ratio of ammonium ion to phosphate ion. The overhead stream exits second quench tower 21 via line 4 into conventional recovery and purification sections (not shown) for subsequent recovery of commercially pure nitrile monomer, the corresponding alkyl nitrile (i.e. acetonitrile or methacetonitrile) and hydrogen cyanide.

At least a portion of the ammonium phosphate solution, or second quench bottoms solution, may be, and preferably is, re-circulated through second quench tower 21 (re-circulation loop not shown in the FIG. 1) until the ratio of ammonium ions ($NH_4^+$) to phosphate ions ($PO_4^{-3}$) is at least about 1.0 and, preferably, not more than about 1.3, and then collected from the bottom of second quench tower 21 and pass via line 5 to the first quench tower 20 as first quench liquid. Such re-circulation can be accomplished by, for example, using another line to direct at least a portion of the second quench bottoms solution in line 5 to the upper portion of second quench tower 21 through, for example, line 14.

The first quench bottom solution comprising aqueous ammonium phosphate exiting the bottom of first quench tower 20 will be passed via line 3 to quench stripper 22 and stripped of volatile residual compounds with a stripping gas passed via line 6 into quench stripper 22. Preferably, the stripping gas will comprise at least one gas selected from the group consisting of propane, nitrogen, carbon dioxide, and carbon monoxide. The stripper overhead comprising stripping gas and said volatile residual compounds will be passed via line 7 to second quench tower 21 for further recovery of useful components.

The stripped quench bottoms are passed from the quench stripper column 22 via line 8 to phosphate decomposer 23, where the diammonium phosphate component of the stripped bottoms is decomposed by heating under a pressure of up to about 900 psig, preferably about 300 to about 600 psig, to an elevated temperature (100° C. to 300° C.), generating a vapor stream comprising ammonia and water together with an aqueous solution of monoammonium phosphate.

The vapor stream is collected from phosphate decomposer 23 as overhead and passed via line 10 to an ammonia stripper 24. The ammonia passes from ammonia stripper 24 as overhead via line 11 to ammonia reclaimer 25, providing ammonia, such as substantially anhydrous ammonia, for recycle to the ammoxidation reactor via line 12. Water recovered as bottoms exits ammonia stripper 24 by line 13 and may be combined with water exiting the ammonia reclaimer 25 via line 15 for recycle or disposal.

The regenerated monoammonium phosphate solution exiting as bottoms from phosphate decomposer 23 will comprise lean aqueous ammonium phosphate solution having a ratio of ammonium ions ($NH_4^+$) to phosphate ions ($PO_4^{-3}$) of at least about 0.7, suitably in a range from about 0.7 to about 1.3, preferably from about 0.9 and about 1.2, more preferably from about 1.0 to about 1.1, and a pH in the range of from about 2.8 to no greater than 6.0, preferably from 2.8 to about 5.8.

The decomposer bottoms are passed via line 14 to second quench tower 21 for recycle as second quench liquid. The level of contaminants in the stream may be lowered by passing a portion of the decomposer bottoms, in admixture with a source of molecular oxygen such as air fed by line 9, to wet oxidation reactor 26 via line 16 under typical wet oxidation process conditions and optionally including an oxidation catalyst as set forth herein above. The stream, depleted of oxidizable contaminants, is then recombined via line 27 with the balance of the decomposer bottoms passing to quench tower 21 via line 14.

Figure 2:
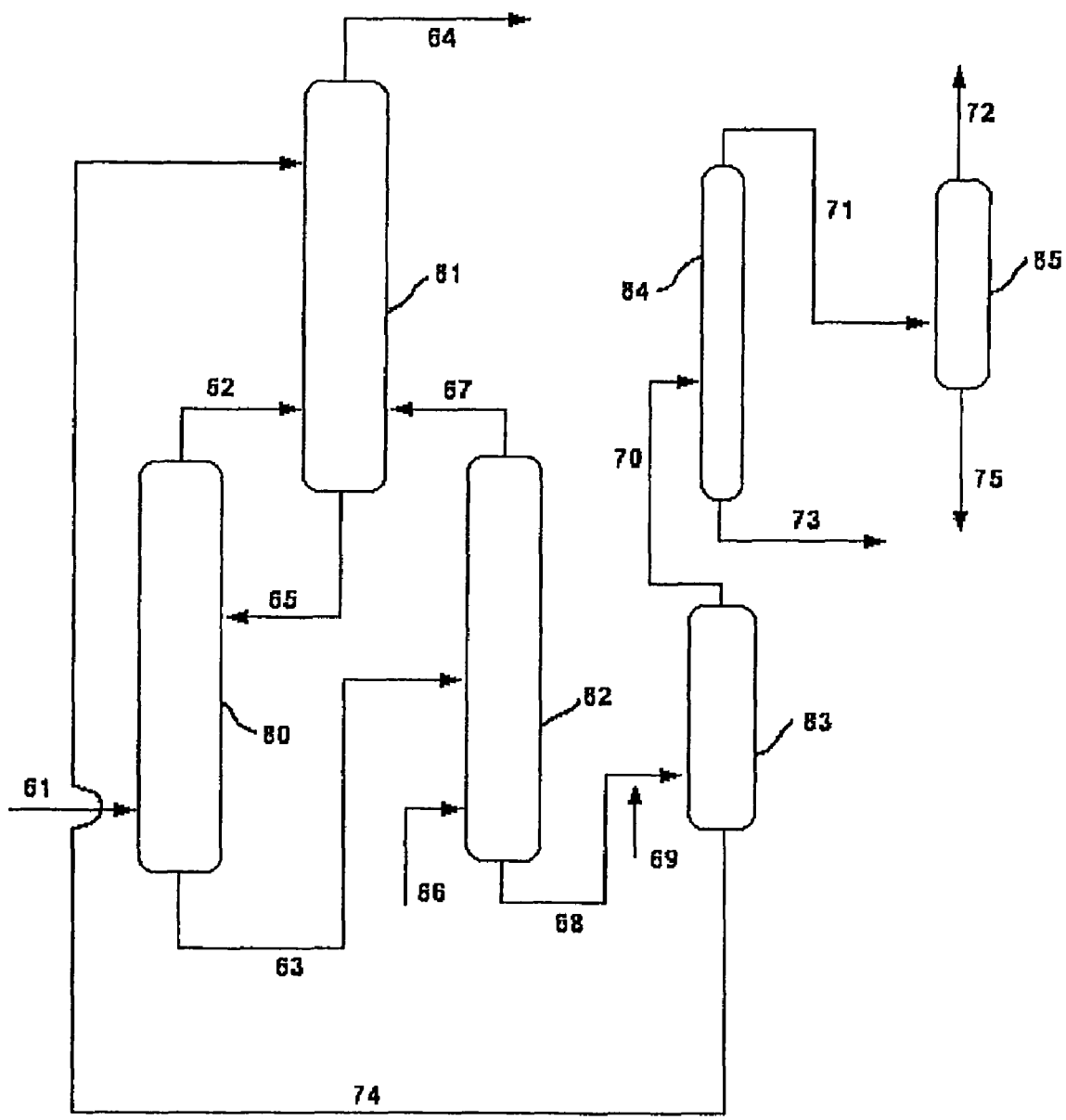
FIG. 2 is a flow diagram of a preferred embodiment of an ammonia recovery process wherein a reactor effluent is quenched in two stages and the ammonium phosphate solution is thermally regenerated in a wet oxidation reactor.

Turning now to the drawing, FIG. 2, there is shown a flow diagram of a further embodiment of the invented two-stage quench process, wherein the diammonium phosphate solution is decomposed and subjected to wet oxidation in a single vessel. As seen in FIG. 2, effluent from an ammoxidation reactor (not shown) is passed via line 61 into a first quench tower 80. In first quench tower 80 the reactor effluent comprising nitrile monomer and unreacted ammonia is contacted with a first quench liquid fed by line 65. The first quench liquid, comprising of ammonium phosphate solution having a ratio of ammonium ions ($NH_4^+$) to phosphate ions ($PO_4^{-3}$) of at least about 1.3 but not more than about 2, absorbs and removes ammonia from the effluent and produces an overhead stream of depleted effluent comprising crude nitrile monomer and residual ammonia, and a first quench bottom solution containing enriched ammonium phosphate solution having an increased ratio of ammonium ion to phosphate ion. The depleted effluent stream passes by line 62 to a second quench tower 81; the first quench bottom solution exits the bottom of first quench tower 80 and passes via line 63 to a quench stripper 82. Although not shown in FIG. 2, at least a portion of the first quench liquid can, and preferably is, re-circulated within first quench tower 80 by, for example, using another line to direct at least a portion of the first quench bottom solution in line 63 to the upper portion of first quench tower 80 through, for example, line 65.

The overhead or depleted effluent stream entering second quench tower 81 via line 62 is contacted with a second quench liquid (recirculating line not shown) fed by line 74. This second quench liquid, comprised of ammonium phosphate solution having an ammonium ion ($NH_4^+$) to phosphate ion ($PO_4^{-3}$) ratio of at least about 0.7, in a range from about 0.7 to about 1.3, and preferably about 1.0-1.1, absorbs the residual ammonia and produces an overhead stream comprising crude nitrile monomer and an ammonium phosphate solution having an increased ratio of ammonium ion to phosphate ion. The overhead stream exits quench tower 81 via line 64 into conventional recovery and purification sections (not shown) for subsequent recovery of commercially pure nitrile monomer, the corresponding alkyl nitrile (i.e. acetonitrile or methacetonitrile) and hydrogen cyanide.

The ammonium phosphate solution, or second quench bottoms solution, having a ratio of ammonium ions ($NH_4^+$) to phosphate ions ($PO_4^{-3}$) of at least about 1.0 but not more than about 1.3, and preferably about 1.0 to about 1.1, will be collected from the bottom of second quench tower 81 and pass via line 65 to the first quench tower 80 for recycle as first quench liquid ammonium phosphate solution. At least a portion of the second quench bottoms solution, may be, and preferably is, re-circulated through second quench tower 81 (re-circulation loop not shown in the FIG. 2) until the ratio of ammonium ions ($NH_4^+$) to phosphate ions ($PO_4^{-3}$) is at least about 1.0 but preferably not more than about 1.3. Such re-circulation can be accomplished by, for example, using another line to direct at least a portion of the second quench bottoms solution in line 65 to the upper portion of second quench tower 81 through, for example, line 74.

A stripping gas, preferably selected from the group consisting of propane, nitrogen, carbon dioxide, carbon monoxide and mixtures thereof, is passed via line 66 into stripper 82 to remove volatile residual compounds including nitrile monomer, hydrogen cyanide, and alkyl nitrile from the first quench bottoms. The stripper overhead comprising stripping gas and said volatile residual compounds exits via line 67 and is recycled to second quench tower 81 for further recovery of useful components.

The stripped quench bottoms are passed from the stripper column 82 via line 68, combined with a source of molecular oxygen such as air, fed by line 69, and fed to a wet oxidation reactor 83, where unwanted organic oxidizable contaminants contained in the stripped quench bottoms are destroyed utilizing typical wet oxidation conditions and, optionally, an oxidation catalyst as set forth herein above.

Typically, wet oxidation is carried out at a pressure of from about 600 to 3000 psig and a temperature of from about 200° C. to 650° C. Heating the stripped quench bottoms comprising the enriched ammonium phosphate solution in the wet oxidation process thermally decomposes the diammonium phosphate to monoammonium phosphate, generating a vapor stream comprising ammonia and water together with an aqueous solution of monoammonium phosphate.

The vapor stream is collected overhead and passed via line 70 to ammonia stripper 84. The ammonia collected from ammonia stripper 84 as overhead is passed via line 71 to ammonia reclaimer 85, providing ammonia, such as substantially anhydrous ammonia, for recycle to the ammoxidation reactor via line 72. Water recovered as bottoms exits ammonia stripper 84 by line 73 and may be combined with water exiting the reclaimer 85 via line 75 for recycle or disposal.

The regenerated monoammonium phosphate solution exiting as bottoms from the oxidation reactor will comprise lean aqueous ammonium phosphate solution having a ratio of ammonium ions ($NH_4^+$) to phosphate ions ($PO_4^{-3}$) of at least about 0.7, suitably in a range from about 0.7 to about 1.3, preferably from about 0.9 and about 1.2, and more preferably from about 1.0 to about 1.1, and a pH in the range of from about 2.8 to no greater than 6.0, preferably from 2.8 to about 5.8.

The oxidation reactor bottoms are passed from wet oxidation reactor 83 to second quench tower 81 via line 74 for recycle as second quench liquid.

In a further embodiment, more fully described and characterized below in connection with FIG. 3, liquid-liquid extraction means will be employed to extract contaminants contained in the aqueous first quench bottoms from the first quench tower. Removing the heavy organics from the quench liquid by solvent extraction obviates the need for a wet oxidation step, thereby reducing costs. In addition, substantially all of the residual organic contaminants that remain after extraction may be removed from the aqueous phase by stripping before passing to the decomposer, reducing the level of contaminants reaching the overhead ammonia and water vapor stream from the thermal decomposition.

A wide variety of means for liquid-liquid extraction are well known in the art, including static columns, agitated columns, pulsed columns, centrifugal contactors and the like. Most such extractors may be adapted for use in the invented process as will be readily apparent to those skilled in the art.

Solvents suitable for use in the practice of this invention will be liquid under the operating conditions and substantially immiscible with the aqueous quench liquid, and will necessarily be a solvent for the contaminants, particularly the heavy organics, present in the quench liquid. Liquid $C_3$-$C_{12}$ hydrocarbons including alkanes and alkanes such as, for example, propane, propane, isobutane and the like; cycloalkanes such as cyclopentane, cyclohexane and the like; and aromatic hydrocarbons including benzene, toluene, xylenes and the like may be found suitable for these purposes. Nitriles that are sparingly soluble in aqueous ammonium phosphate solutions, particularly at high salt concentrations, may also be suitable for these purposes. For example, alkyl nitriles such as, for example, acrylonitrile, acetonitrile, and methacrylonitrile are suitable. Acetonitrile and methacetonitrile, and nitrile monomers such as acrylonitrile or methacrylonitrile, are immiscible with aqueous phosphate solutions, volatile under the operating conditions, readily compatible with product recovery steps employed in the process and may be found particularly desirable for this use, alone or in any combination.

The raffinate, i.e. the extracted aqueous quench bottoms will be stripped to remove residual solvent before being heated to recover ammonia and regenerate aqueous ammonium phosphate. If necessary, the regenerated phosphate solution may then be passed to an evaporator to remove excess water before being recycled as second quench liquid.

The extract, i.e. the organic phase containing solvent, dissolved organic components and water, will be rectified by distillation using conventional distillation means to recover solvent and desirable co-products. The still bottoms will contain heavy organics with substantial fuel value, and may be conveniently disposed of by incineration, preferably with recovery of heat.

Figure 3:
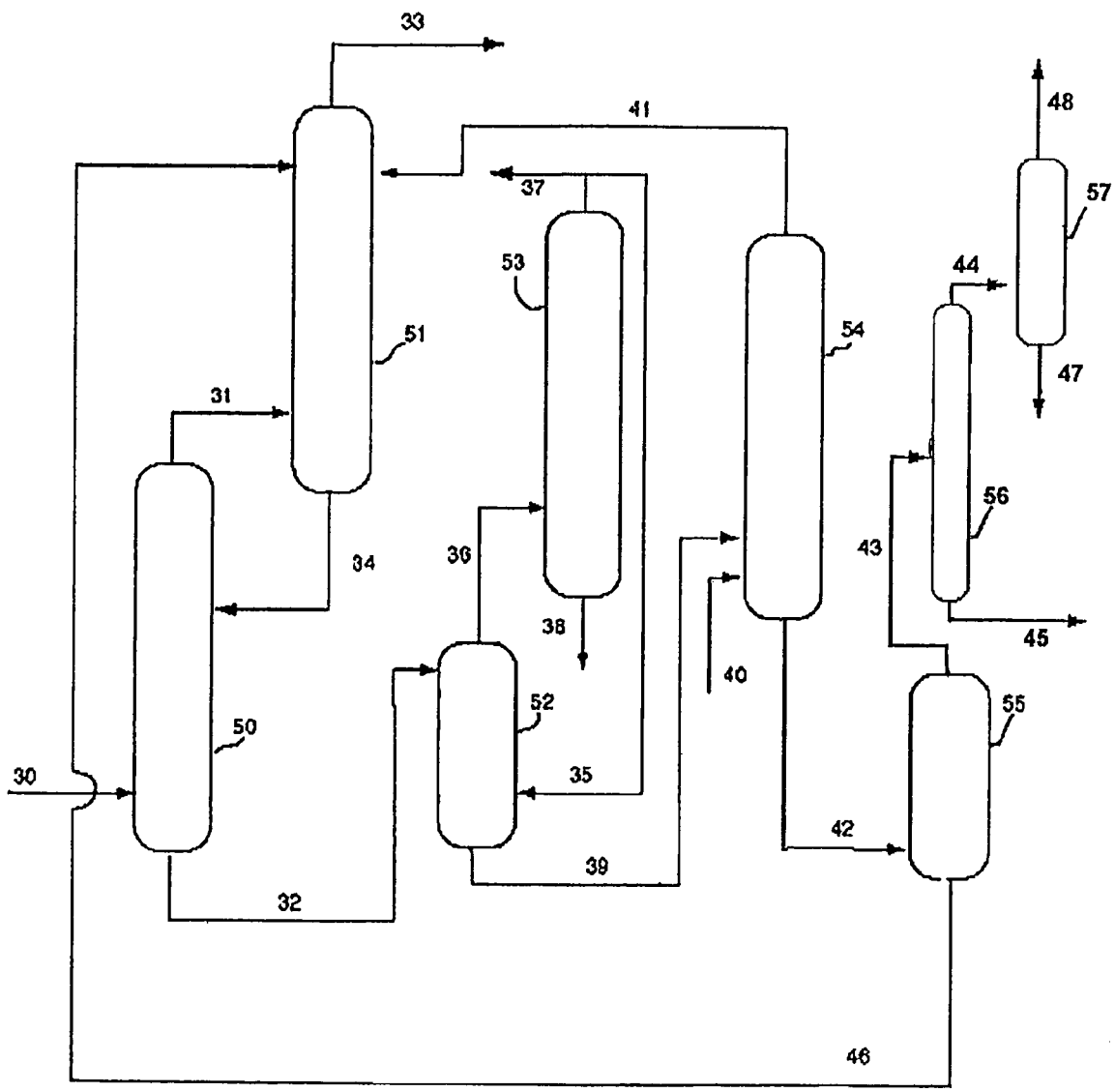
FIG. 3 is a flow diagram of a preferred embodiment of an ammonia recovery process wherein a reactor effluent is quenched in two stages and the organic contaminants are removed from the quench bottoms by solvent extraction prior to thermally regenerating the ammonium phosphate solution for recycle.

Turning now to the drawing, FIG. 3, showing a flow diagram of a two-stage quench process with subsequent solvent extraction and stripping of the quench liquid and recovery of the captured ammonia. As seen in FIG. 3, effluent from an ammoxidation reactor (not shown) is passed via line 30 into a first quench tower 50. In first quench tower 50 the reactor effluent comprising nitrile monomer and unreacted ammonia is contacted with a first quench liquid fed by line 34. The first liquid, comprising of ammonium phosphate solution having a ratio of ammonium ions ($NH_4^+$) to phosphate ions ($PO_4^{-3}$) of at least about 1.3 but not more than about 2, absorbs and removes ammonia from the effluent and produces an overhead stream of depleted effluent comprising crude nitrile monomer and residual ammonia, and a first quench bottom solution containing enriched ammonium phosphate solution having an increased ratio of ammonium ion to phosphate ion. The depleted effluent stream passes by line 31 to a second quench tower 51; the first quench bottom solution exits quench tower 50 and passes via line 32 to a liquid-liquid extractor 52. Although not shown in FIG. 3, at least a portion of first quench liquid can, and preferably is, re-circulated within first quench tower 50 by, for example, using another line to direct at least a portion of the first quench bottom solution in line 32 to the upper portion of first quench tower 50 through, for example, line 34.

The overhead or depleted effluent stream entering second quench tower 51 via line 31 is contacted with a second quench liquid fed by line 46. This second quench liquid, comprising of ammonium phosphate solution having an ammonium ion ($NH_4^+$) to phosphate ion ($PO_4^{-3}$) ratio of at least about 0.7, preferably in a range from about 0.7 to about 1.3, and preferably about 1.0 to about 1.1, absorbs the residual ammonia and produces an overhead stream comprising crude nitrile monomer and an ammonium phosphate solution having an increased ratio of ammonium ion to phosphate ion. The overhead stream exits quench tower 51 via line 33 into conventional recovery and purification sections (not shown) for subsequent recovery of commercially pure nitrile monomer, the corresponding alkyl nitrile (i.e. acetonitrile or methacetonitrile) and hydrogen cyanide. At least a portion of the second quench bottoms solution, may be, and preferably is, re-circulated through second quench tower 51 (re-circulation loop not shown in FIG. 3) until the ratio of ammonium ions ($NH_4^+$) to phosphate ions ($PO_4^{-3}$) is at least about 1.0. Such re-circulation can be accomplished by, for example, using another line to direct at least a portion of the second quench bottoms solution in line 34 to the upper portion of second quench tower 51 through, for example, line 46.

The ammonium phosphate solution, or second quench bottoms solution, having a ratio of ammonium ions ($NH_4^+$) to phosphate ions ($PO_4^{-3}$) of at least about 1.0 but not more than about 1.3, preferably 1.0 to about 1.1, will be collected from the bottom of second quench tower 51 and passed via line 34 to the first quench tower 50 for recycle as first quench liquid ammonium phosphate solution.

Solvent, fed to the extractor via line 35, contacts the first quench bottoms stream counter currently, absorbing the organic components from the aqueous enriched ammonium phosphate solution. The immiscible organic phase or extract separated from the aqueous phase exits the extractor via line 36 and is fed to distillation means, solvent recovery tower 53. The extract is fractionated to recover solvent for recycle to extractor 52 via line 35; volatile residuals including hydrogen cyanide and alkyl nitrile exit solvent recovery tower 53 via line 37 for further recovery of useful components, for example by recycle to first quench tower 50. The still bottoms containing heavy organic contaminants, including polymers, exit the still via line 38. These may be incinerated or otherwise disposed of as waste, if desired.

The aqueous phase or raffinate will exit the extractor and be fed via line 39 to stripper 54. A stripping gas, preferably selected from the group consisting of propane, nitrogen, carbon dioxide, carbon monoxide and mixtures thereof, is fed via line 40 to the bottom of stripper 54, rising through the raffinate to remove residual solvent. The stripper overhead comprising stripping gas and said volatile residual solvent exits via line 41 and may be recycled to second quench tower 51 as shown for further recovery of useful components.

The stripped raffinate is passed from stripper 54 via line 42 to phosphate decomposer 55. In phosphate decomposer 55, the diammonium phosphate present in the stripped raffinate is converted to free ammonia and monoammonium phosphate by heating under a pressure of up to about 900 psig, preferably in a range of about 300 to about 600 psig, to an elevated temperature (about 100° C. to about 300° C.), generating a vapor stream containing ammonia and water together with an aqueous solution of monoammonium phosphate. Oxygen from, for example, a molecular oxygen-containing gas, such as air, may be present but is not required.

The vapor stream is collected overhead and passed via line 43 to an ammonia stripper 56. The ammonia passes from ammonia stripper 56 as overhead and is passed via line 44 to ammonia reclaimer 57, providing ammonia, such as substantially anhydrous ammonia, for recycle to the reactor via line 48. Water recovered as bottoms exits ammonia stripper 56 by line 45 and may be combined with water exiting the reclaimer 57 via line 47 for recycle or disposal.

The regenerated monoammonium phosphate solution exiting as bottoms from phosphate decomposer 55 will comprise lean aqueous ammonium phosphate solution having a ratio of ammonium ions ($NH_4^+$) to phosphate ions ($PO_4^{-3}$) of at least about 0.7, suitably in a range from about 0.7 to about 1.3, preferably from about 0.9 and about 1.2, more preferably from about 1.0 to about 1.1, and a pH in the range of from about 2.8 to no greater than 6.0, preferably from 2.8 to about 5.8.

The monoammonium phosphate solution from phosphate decomposer 55 passes via line 46 to second quench tower 51 for recycle as second quench solution after further adjusting pH and ammonium-to-phosphate ratio if required.

The following examples are offered to illustrate particular features of the invention, and are not intended to be limiting in any way.

EXAMPLES

The following Example 1 and Control Example demonstrate the effectiveness of the two-stage quench in removing ammonia from the reactor effluent.

Example 1

The effluent from a bench-scale, fluid-bed ammoxidation reactor comprising a propane ammoxidation catalyst continuously fed with propane, ammonia, oxygen and nitrogen and running at a steady-state condition is fed to a bench-scale, two-stage, spray phosphate quench unit. The quench unit comprises two quench towers, each independently fitted with a phosphate recirculation system including a reservoir containing aqueous ammonium phosphate. The first or stage-one quench tower includes four spray nozzles disposed vertically in the vessel and pointed downward; the second or stage-two quench tower includes one spray nozzle near the top of the vessel, pointed downward.

The aqueous ammonium phosphate in the first-stage reservoir is maintained at a pH 6, and a temperature of 60° C.; the aqueous ammonium phosphate in the second stage reservoir is maintained at pH 4, and a temperature of 60° C.

The hot reactor effluent is fed to the stage-one quench tower near the bottom, flowing upward and contacting the first-stage ammonium phosphate solution fed to the tower through the spray nozzles. The reactor effluent exits the quench tower at the top, and is fed to the stage-two quench tower near the bottom, flowing upward and contacting the second-stage ammonium phosphate solution fed to the tower through the spray nozzle. The reactor effluent then exits the tower at the top and is collected and sampled for analysis.

The concentration of ammonia in the reactor effluent exiting the second-stage is determined to be 0.5% of the concentration in the reactor effluent, demonstrating that a two-stage quench process may capture as much as 99.5% or more of the ammonia present in a process stream.

Control Example 1

The quench process is employed substantially as described in Example 1, but using only the first-stage of the two-stage quench unit. The reactor effluent exiting the tower at the top is collected and sampled for analysis.

The concentration of ammonia in a sample of the reactor effluent exiting the first-stage quench tower is determined to be 4.5% of the concentration in the reactor effluent. In a subsequent sample, the concentration of ammonia is determined to be 5.5% of the concentration in the reactor effluent.

It will thus be apparent that the two-stage quench is substantially more effective than a single-stage process in capturing ammonia from the process stream.

The following Examples 2-4 are provided to demonstrate the use of solvent extraction for removal of organic components from aqueous quench bottoms.

Example 2

A 50 cc sample of stripped aqueous quench bottoms with 27% total dissolved solids and pH 6, taken from the stripper of a pilot-scale propane ammoxidation process carried out substantially as described in U.S. Pat. No. 5,994,299, is extracted with 10 cc of acetonitrile in a separatory funnel. After settling, the upper organic phase is found to contain 51% of the organic components originally present in the stripped aqueous quench bottoms, determined by total carbon content analysis.

Example 3

A further sample, 50 cc, of the stripped aqueous quench bottoms is extracted with 10 cc of acrylonitrile in a separatory funnel substantially as described in Example 2. After settling, the upper organic phase is found to contain 49% of the organic components originally present in the stripped aqueous quench bottoms, determined by total carbon content analysis.

Example 4

A 50 cc sample of aqueous quench bottoms with 27% total dissolved solids and pH 2, taken from the quench tower of a pilot-scale propane ammoxidation process carried out substantially as described in U.S. Pat. No. 5,994,299, is extracted with 10 cc of acetonitrile in a separatory funnel. After settling, the upper organic phase, analyzed for total carbon content, is found to contain 58.9% of the organic components originally present in the aqueous quench bottoms.

The wet oxidation and decomposing of the aqueous phosphate solution, when carried out in a single reactor as described in the embodiment of FIG. 2, will preferably be carried out at temperatures and for times sufficient to completely destroy contaminants present in the aqueous phosphate. When the aqueous phosphate solution is decomposed in a separate step before undergoing wet oxidation using, for example, wet oxidation conditions known in the prior art, residual contaminants and contaminants generated in the decomposition step may distill with the aqueous ammonia stream and then be separated from the ammonia with the water component, contaminating the wastewater. The problem may be avoided by conducting the decomposition at temperatures above 200° C. for extended residence times, thereby destroying the volatile contaminants.

The following Examples 5-7 demonstrate the effect of temperature and residence time on destruction of contaminants commonly found in the quench bottoms of a propylene ammoxidation process, including acrylonitrile, cyanide, fumaronitrile and pyrazole.

Example 5

A one-gallon, stirred autoclave fitted with a throttling valve on the top connected to a condenser was purged with inert gas and charged with ammonium phosphate solution quench bottoms obtained from a propylene ammoxidation process, substantially as described in Example 1. The autoclave was sealed and heated at 204° C. under a pressure of 200-225 psig, with continuous removal of vapors through the throttling valve, for a period of about 60 min. Approximately 60% of the contents were removed as vapor and condensed. The results of the analyses of the feed, condensate and autoclave bottoms for the four contaminants are summarized in the following Table 1.

TABLE 1

| Contaminant | | Feed | Condensate | Bottoms |
|---|---|---|---|---|
| Acrylonitrile | mg/l | 259 | <1 | 6.9 |
| Cyanide | mg/l | 8.8 | <2 | <2 |

TABLE 1-continued

| Contaminant | | Feed | Condensate | Bottoms |
|---|---|---|---|---|
| Fumaronitrile | mg/l | 747 | <5 | <5 |
| Pyrazole | mg/l | 1096 | 1191 | 1138 |

Example 6

A one-gallon, stirred autoclave fitted with a throttling valve on the top connected to a condenser was purged with inert gas and charged with ammonium phosphate solution quench bottoms obtained as in Example 5. The autoclave was sealed and heated at 232° C. under a pressure of 350-400 psig, with continuous removal of vapors through the throttling valve, for a period of about 60 min. Approximately 60% of the contents were removed as vapor and condensed. The results of the analyses of the feed, condensate and autoclave bottoms for the four contaminants are summarized in the following Table 2.

TABLE 2

| Contaminant | | Feed | Condensate | Bottoms |
|---|---|---|---|---|
| Acrylonitrile | mg/l | 41 | <1 | 31 |
| Cyanide | mg/l | 896 | <2 | 65 |
| Fumaronitrile | mg/l | 2645 | <10 | 240 |
| Pyrazole | mg/l | 35 | 68 | 103 |

Example 7

A stripping tower, two inches in diameter, eight feet in height and containing mesh packing, fitted with an overhead condenser/receiver and a steam heated reboiler, was fed continuously with ammonium phosphate solution quench bottoms obtained as in Example 4, heated at 150° C. at a pressure of 60 psig. Approximately 30% of the feed was evaporated and collected in the receiver as overhead condensate. The results of the analyses of the feed, condensate and autoclave bottoms for two contaminants, acrylonitrile and cyanide are summarized in the following Table 3.

TABLE 3

| Contaminant | | Feed | Condensate | Bottoms |
|---|---|---|---|---|
| Acrylonitrile | mg/l | 2.3 | <1 | 6.9 |
| Cyanide | mg/l | 220 | 45 | 150 |

Example 8

A pilot-plant scale ammonia recovery system, based on the design shown in FIG. 1, was used for this example. An effluent slipstream from a commercial propylene-based acrylonitrile manufacturing plant was used with appropriate amounts of ammonia, carbon dioxide and water added to simulate the effluent composition of a propane based fluid bed ammoxidation reactor. This simulated effluent was fed to the pilot-plant scale downstream quench system, yielding the data shown in Tables 4a and 4b for the two-stage quench and quench stripper as described hereinabove. These data show that the invented process on a pilot-plant scale resulted in greater than 99.5% recovery efficiencies for ammonia and acrylonitrile, greater than 95% recovery efficiency for hydrogen cyanide and better than 83% acetonitrile recovery efficiency as shown by the data in Table 4a. The impact of increased stripper gas flow rate and operating temperature is demonstrated by significant reductions in acrylonitrile, hydrogen cyanide and acetonitrile in the stripped bottoms stream as shown by the data in Table 4b. In the Tables below, PBW means "parts by weight."

TABLE 4a

| | Period #1 | Period #2 |
|---|---|---|
| 1st Stage Quench | | |
| Feed in (PBW/hr) | 4,650 | 4,370 |
| Sump temp (F.) | 153 | 151 |
| pH | 6.1 | 6.2 |
| 2nd Stage Quench | | |
| Sump temp (F.) | 143 | 142 |
| pH | 4.5 | 4.5 |
| Quench Stripper | | |
| Stripper gas flow (PBW/hr) | 28 | 30 |
| Stripper gas temp (F.) | 199 | 200 |
| Recovery Efficiency (wt %) | | |
| Ammonia | >99.5 | >99.5 |
| Acrylonitrile | 99.6 | 99.5 |
| HCN | 95.3 | 95.4 |
| Acetonitrile | 83.8 | 83.0 |

TABLE 4b

| | Period #2 | Period #3 |
|---|---|---|
| 1st Stage Quench | | |
| Feed in (PBW/hr) | 4,370 | 4,600 |
| Sump temp (F.) | 151 | 155 |
| pH | 6.2 | 6.1 |
| 2nd Stage Quench | | |
| Sump temp (F.) | 142 | 145 |
| pH | 4.5 | 4.7 |
| Quench Stripper | | |
| Stripper gas flow (PBW/hr) | 30 | 150 |
| Stripper gas temp (F.) | 200 | 226 |
| Stripped Bottoms (ppm) | | |
| Acrylonitrile | 350 | 64 |
| HCN | 754 | 516 |
| Acetonitrile | 478 | 108 |

The methods and process steps of the invention are described and illustrated in terms of particular embodiments in connection with the ammoxidation of hydrocarbons in the production of nitrile monomers; however, those skilled in the art will recognize that many alternatives, modifications and variations of the described methods may be found suitable for use in the practice of this invention. Moreover, the methods may be applied to ammonia-containing effluent from other processes. Such modifications and additions, as well as compositions, formulations and apparatus embodying them, are contemplated to lie within the scope of the invention, which is defined and set forth in the following claims.

We claim:

1. A process for the recovery of ammonia from a vaporous stream comprising contacting said stream with a first aqueous ammonium phosphate solution comprising ammonium dihydrogen phosphate and diammonium hydrogen phosphate, having a first ratio of ammonium ions ($NH_4^+$) to phosphate ions ($PO_4^{-3}$), thereby absorbing ammonia from said stream and forming aqueous quench bottoms having increased ratio of ($NH_4^+$) to ($PO_4^{-3}$) and a depleted vapor stream comprising residual ammonia; contacting said depleted vapor stream with a second aqueous ammonium phosphate solution comprising ammonium dihydrogen phosphate and diammonium hydrogen phosphate, and having a second ratio of ammonium ions ($NH_4^+$) to phosphate ions ($PO_4^{-3}$) that is lower than the first ratio, thereby absorbing substantially all of said residual ammonia from said vapor stream and forming said first aqueous ammonium phosphate solution; heating said aqueous quench bottoms to an elevated temperature for a time sufficient to decompose at least a portion of the diammonium phosphate and generate a vaporous ammonia stream; and separating the ammonia from the remaining components of said vaporous ammonia stream.

2. The process of claim 1 wherein the ratio of ammonium ions to phosphate ions in the first aqueous ammonium phosphate solution is greater than about about 1.3.

3. The process of claim 1 wherein the ratio of ammonium ions to phosphate ions in the second aqueous ammonium phosphate solution is from about 0.7 to about 1.3.

4. The process of claim 1 further comprising passing a stripper gas through the aqueous quench bottoms to remove volatile organic components.

5. The process of claim 1 further comprising extracting the aqueous quench bottoms with an immiscible solvent.

6. The process of claim 5 wherein said solvent is selected from nitrile monomers and alkyl nitrites.

7. The process of claim 5 further comprising passing a stripper gas through the extracted aqueous quench bottoms to remove residual solvent.

8. The process of claim 4 or 7 wherein said stripper gas comprises at least one gas selected from the group consisting of propane, nitrogen, carbon dioxide, and carbon monoxide.

9. The process of claim 1 wherein said aqueous quench bottoms are heated for a time sufficient to reduce the ratio of ratio of ammonium ions ($NH_4^+$) to phosphate ions ($PO_4^{-3}$) to a value in the range of from about 0.7 to about 1.3.

10. The process of claim 9 further comprising heating said aqueous quench bottoms under wet oxidation conditions.

11. The process of claim 1 wherein said aqueous quench bottoms are heated for a time sufficient to reduce the ratio of ammonium ions ($NH_4^+$) to phosphate ions ($PO_4^{-3}$) to a value in the range of from about 0.7 to about 1.3, subjected to wet oxidation, and recycled as said second aqueous ammonium phosphate solution.

12. The process of claim 1 wherein said aqueous quench bottoms are heated under wet oxidation conditions in a wet oxidation reactor for a time sufficient to reduce the ratio of ammonium ions ($NH_4^+$) to phosphate ions ($PO_4^{-3}$) to a value in the range of from about 0.7 to about 1.3, and recycled as said second aqueous ammonium phosphate solution.

13. The process of claim 1 wherein the ammonium ion to phosphate ion ratio in the first aqueous ammonium phosphate solution is from about 1.3 to about 2.

14. The process of claim 1 wherein the pH of the second aqueous ammonium phosphate solution is from about 2.5 to about 4.5.

15. The process of claim 1 wherein the pH of the second aqueous ammonium phosphate solution is from 3 to about 4.

16. The process of claim 1 wherein the pH of the first aqueous ammonium phosphate solution is from about 5 to about 7.

17. In a process for the recovery of unreacted ammonia from a reactor effluent obtained from an ammoxidation reaction zone for the production of an unsaturated nitrile, said process comprising the steps of quenching said reactor effluent with an aqueous ammonium phosphate solution, thereby absorbing unreacted ammonia present in the reactor effluent and forming an ammonia-enriched aqueous solution richer in ammonium ions than said aqueous ammonium phosphate solution; heating said ammonia-enriched aqueous solution to an elevated temperature sufficient to reduce the amount of ammonium ions, thereby regenerating said aqueous ammonium phosphate solution and generating a vaporous stream containing ammonia; and recycling said vaporous stream to the ammoxidation reaction zone, the improvement comprising quenching said reactor effluent with a first aqueous ammonium phosphate solution comprising ammonium dihydrogen phosphate and diammonium hydrogen phosphate wherein the ratio of ammonium ions ($NH_4^+$) to phosphate ions ($PO_4^{-3}$) is greater than 1.3, thereby absorbing greater than about 90% of the unreacted ammonia present in the reactor effluent and forming said ammonia-enriched solution and depleted effluent comprising residual ammonia; and contacting said depleted effluent with a second aqueous ammonium phosphate solution comprising ammonium dihydrogen phosphate and diammonium hydrogen phosphate wherein the ratio of ammonium ions ($NH_4^+$) to phosphate ions ($PO_4^{-3}$) is from about 0.7 to about 1.3, thereby absorbing said residual ammonia from said reactor effluent and forming said first aqueous ammonium phosphate solution.

18. The process of claim 17 wherein the improvement further comprises extracting said ammonia-enriched solution with an immiscible solvent to remove solvent-soluble soluble contaminants and stripping the extracted solution to remove residual solvent prior to heating ammonia-enriched solution and generating said vaporous stream.

19. The process of claim 17 wherein the improvement further comprises heating said ammonia-enriched solution under wet oxidation conditions to an elevated temperature for a time sufficient to destroy at least a portion of contaminants contained therein and reduce the amount of ammonium ions, thereby regenerating said aqueous ammonium phosphate solution and generating said vaporous stream.

20. The process of claim 17 wherein the improvement comprises quenching said reactor effluent with a first aqueous ammonium phosphate solution comprising ammonium dihydrogen phosphate and diammonium hydrogen phosphate wherein the ratio of ammonium ions ($NH_4^+$) to phosphate ions ($PO_4^{-3}$) is greater than 1.3, thereby absorbing greater than about 90% of the unreacted ammonia present in the reactor effluent and forming said ammonia-enriched aqueous solution and a depleted effluent comprising residual ammonia; contacting said depleted effluent with a second aqueous ammonium phosphate solution comprising ammonium dihydrogen phosphate and diammonium hydrogen phosphate wherein the ratio of ammonium ions ($NH_4^+$) to phosphate ions ($PO_4^{-3}$) is from about 0.7 to about 1.3, thereby absorbing said residual ammonia from said reactor effluent and forming said first aqueous ammonium phosphate solution; extracting said ammonia-enriched aqueous solution with an immiscible solvent to remove solvent-soluble contaminants; stripping the extracted ammonia-enriched aqueous solution to remove residual solvent; heating said ammonia-enriched aqueous solution to an elevated temperature sufficient to reduce the amount of ammonium ions, thereby regenerating said aqueous ammonium phosphate solution and generating a vaporous stream containing ammonia; stripping said vaporous stream to separate ammonia and contaminants, and dehydrating said ammonia prior to recycle.

21. The process of claim 17 wherein the vaporous stream recycled to the ammoxidation reaction zone comprises anhydrous ammonia.

22. The process of claim 1 wherein the ratio of ammonium ions to phosphate ions in the second aqueous ammonium phosphate solution is greater than about 0.9 to about 1.2.

23. The process of claim 1 wherein the ratio of ammonium ions to phosphate ions in the second aqueous ammonium phosphate solution is from about 1.0 to about 1.1.

* * * * *